(12) United States Patent
Barley et al.

(10) Patent No.: US 11,810,661 B2
(45) Date of Patent: Nov. 7, 2023

(54) VESSEL ANNOTATOR

(75) Inventors: Maya Ella Barley, Walton on Thames (GB); Thijs Elenbaas, Nijmegen (NL); Raoul Florent, Velle D'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 667 days.

(21) Appl. No.: 14/342,469

(22) PCT Filed: Aug. 29, 2012

(86) PCT No.: PCT/IB2012/054430
§ 371 (c)(1),
(2), (4) Date: Mar. 3, 2014

(87) PCT Pub. No.: WO2011/045700
PCT Pub. Date: Apr. 21, 2011

(65) Prior Publication Data
US 2015/0082143 A1    Mar. 19, 2015

Related U.S. Application Data

(60) Provisional application No. 61/533,817, filed on Sep. 13, 2011.

(51) Int. Cl.
*G06F 40/169* (2020.01)
*G16H 30/40* (2018.01)
(Continued)

(52) U.S. Cl.
CPC ......... *G16H 30/40* (2018.01); *G06F 3/04812* (2013.01); *G06F 3/04842* (2013.01); *G06F 40/169* (2020.01); *G16H 30/20* (2018.01)

(58) Field of Classification Search
CPC ... G16H 30/20; G06F 40/169; G06F 3/04812; G06F 3/04842; G06H 30/40; G06H 30/20
See application file for complete search history.

(56) References Cited

U.S. PATENT DOCUMENTS 6,501,489 B1 * 12/2002 Kobayashi ............ G06F 3/0481
715/764
6,782,284 B1    8/2004 Subramanyan et al.
(Continued)

FOREIGN PATENT DOCUMENTS

| JP | 2010082269 A | 4/2010 |
| WO | 2005031635 A1 | 4/2005 |
| WO | 2010067276 A1 | 6/2010 |

OTHER PUBLICATIONS

Huang et al, "IVME: A Tool for Editing, Manipulation, Quantification, and Labeling of Cerebrovascular Models", Computerized Medical Imaging and Graphics, vol. 30, No. 3, Apr. 1, 2006, pp. 187-195.

(Continued)

*Primary Examiner* — Kyle R Stork (57) ABSTRACT

The present invention relates to annotating a medical image. For an improved manual insertion of information in a medical image, it is provided to display an image (130) of a tubular structure; and to display a graphical representation (132) of at least one segmented portion of the tubular structure; wherein the graphical representation comprises at least one indicator line representing the portion's shape and/or extension; and wherein the graphical representation is displayed in combination with the image of the tubular structure; and to generate and display at least one marker (128) overlaid to the image of the tubular structure; wherein the marker is movable (134) along the graphical representation; and to position the marker at a location along the graphical representation to indicate a predetermined feature of the tubular structure.

21 Claims, 5 Drawing Sheets

(51) Int. Cl.
*G16H 30/20* (2018.01)
*G06F 3/04812* (2022.01)
*G06F 3/04842* (2022.01)

(56) References Cited

U.S. PATENT DOCUMENTS

| | | | |
|---|---|---|---|
| 7,386,339 B2 | 6/2008 | Strommer | |
| 7,706,589 B2 | 4/2010 | Rasche | |
| 8,505,978 B1* | 8/2013 | Leon | G07B 17/00024 |
| | | | 283/67 |
| 9,741,129 B2* | 8/2017 | Holtz | G06T 7/20 |
| 2004/0066369 A1* | 4/2004 | Rosenberg | B25J 9/1689 |
| | | | 345/156 |
| 2004/0234933 A1* | 11/2004 | Dawson | G09B 23/28 |
| | | | 434/262 |
| 2005/0107688 A1 | 5/2005 | Strommer | |
| 2006/0050941 A1 | 3/2006 | Middleton et al. | |
| 2006/0061595 A1* | 3/2006 | Goede | G06F 17/241 |
| | | | 345/619 |
| 2006/0074285 A1 | 4/2006 | Zarkh | |
| 2008/0287909 A1* | 11/2008 | Viswanathan | A61B 17/3478 |
| | | | 604/506 |
| 2008/0317195 A1 | 12/2008 | Kobayashi | |
| 2010/0094124 A1 | 4/2010 | Schoonenberg | |
| 2010/0128963 A1 | 5/2010 | Waku et al. | |

OTHER PUBLICATIONS

Mortensen et al, "Interactive Segmentation With Intelligent Scissors", CVGIP Graphic Models and Image Processing, vol. 60, No. 5, Sep. 1, 1998, pp. 349-384.

* cited by examiner

VESSEL ANNOTATOR

CROSS-REFERENCE TO PRIOR APPLICATIONS

This application is the U.S. National Phase application under 35 U.S.C. § 371 of International Application Serial No. PCT/IB2012/054430, filed on Aug. 29, 2012, which claims the benefit of U.S. application Ser. No. 61/533,817, filed on Sep. 13, 2011. These applications are hereby incorporated by reference herein.

FIELD OF THE INVENTION

The present invention relates to an annotating device for annotating a medical image, a medical X-ray imaging system, a method for annotating a medical image, a computer program element and a computer readable medium.

BACKGROUND OF THE INVENTION

During medical examination and intervention procedures, medical images may be provided with markers or notes by a user indicating locations of features of a tubular structure. For example, during a stent grafting procedure, a surgeon uses a white board marker to draw side branches of a vessel on a monitor screen in order to ensure accurate positioning of the stent graft, and in particular to make sure that blood flow to side branch arteries is not blocked. The borders or axes of the side branches marked on the monitor screen can then serve as a guide while positioning the stent graft. However, it has been shown that making such notes on a monitor screen can be cumbersome and time consuming for the clinician.

SUMMARY OF THE INVENTION

Thus, there is a need for an improved manual insertion of information in a medical image.

The object of the present invention is solved by the subject-matter of the independent claims, wherein further embodiments are incorporated in the dependent claims.

It should be noted that the following described aspects of the invention apply also for the annotating device, the medical X-ray imaging system, the method for annotating a medical image, as well as for the computer program element and the computer readable medium.

According to a first aspect of the present invention, a method for annotating a medical image is provided, comprising the following steps:
  a) displaying an image of a tubular structure;
  b) displaying a graphical representation of at least one segmented portion of the tubular structure, wherein the graphical representation comprises at least one indicator line representing the portion's shape and/or extension, and wherein the graphical representation is displayed in combination with the image of the tubular structure;
  c) generating and displaying at least one marker overlaid on the image of the tubular structure, wherein the marker is movable along the graphical representation; and
  d) positioning the marker at a location along the graphical representation to indicate a predetermined feature of the tubular structure.

According to an aspect of the invention, the graphical representation is shown in addition to an image of the tubular structure in order to provide the possibility for the user to use the image shown for further information. For example, the user can interpret the image shown based on his experience. Thus, features can be detected, and marked by positioning the marker accordingly, also in cases where automatic detection algorithms fail to be precise and reliable enough. In other words, instead of just showing the result of an algorithm, for example, a segmented structure, i.e. a structure based on interpretation of image data, the information provided to the user contains both already interpreted or processed data in form of the graphical representation as well as further image data, e.g. raw image data, for further interpretation. Thus, the annotation according to the invention also makes use of and exploits the user's knowledge and experience and skills to detect certain features that may be hardly visible.

According to an aspect of the invention, the tubular structure is a vascular structure. The tubular structure can also be an air tract of an object, for example. The tubular structure can also refer to a urinal tract.

According to an aspect of the invention, the tubular structure is a vascular structure and the segmented portion is a segmented vessel.

According to an exemplary embodiment of the invention, in step c) the at least one marker is generated and initially positioned automatically next to the graphical representation.

The at least one marker may initially be positioned in an automatic manner, i.e. without the need for user interaction, in relation to the graphical representation. Thus, the automatic positioning takes place before the user starts with any adjustment of the marker's position. Simply said, the system makes an initial proposal and already positions the marker on the graphical representation. For example, the marker is initially positioned at least partly outside the graphical representation overlaid on the displayed imaged of the tubular structure. In other words, the user can then directly start with the positioning of the marker to a location of a feature to be indicated.

For example, the marker is positioned and shown near the graphical representation.

The at least one marker may initially be positioned in an automatic way alongside or along the graphical representation, i.e. adjacent to the graphical representation, adjoining or joined to the graphical representation. For example, the marker is positioned attached to the graphical representation, i.e. close-by or nearby or in vicinity to the graphical representation.

For example, for the automatic positioning, a location with a high probability of a predetermined feature may be determined and the marker is initially positioned at the provided location.

The marker may be positioned at best guess for a location of a predetermined feature, wherein the marker may be initially positioned in contact with the graphical representation, but on the side of the latter.

According to an exemplary embodiment of the invention, the movement possibilities of the marker in relation to the displayed image are restricted at least in one dimension, wherein the restriction is related to the graphical representation.

According to an exemplary embodiment of the invention, the marker is a 2D-marker with a perpendicular orientation in relation to the respective portion of the at least one segmented portion, wherein the 2D-marker is slideable along the segmented portion, e.g. along a segmented vessel.

According to an exemplary embodiment of the invention, the marker is a 3D-marker arrow with a spatial orientation in relation to the at least one segmented portion, wherein the 3D-arrow is slideable along the segmented portion and rotatable around the portion, such as a segmented vessel.

According to an exemplary embodiment of the invention, the predetermined feature is a bifurcation of a (sub-) branch of the tubular structure.

In case of a vascular structure, the predetermined feature may be at least one of the group of an aneurysm, a calcification within the vascular structure, a device placed inside the vascular structure, a dissection of the vessel, a lesion, a stenosis, and a thrombosis.

According to an exemplary embodiment of the invention, the image of the tubular, structure, e.g. vascular structure, is a fluoroscopy structure.

The image may be a 3D-image of the tubular/vascular structure.

According to an exemplary embodiment, the segmented portion is provided with a portion outline. For example, the segmented vessel is provided with a vessel outline.

The graphical representation may be displayed overlaid to the image of the tubular structure.

According to a second aspect of the invention, an annotating device for annotating a medical image is provided, comprising a processing unit, a display unit, and an interface unit. The processing unit is configured to generate at least one marker overlaid to an image of a tubular structure, wherein the marker is movable along the graphical representation. The display unit is configured to display an image of a tubular structure, and to display a graphical representation of at least one segmented portion of the tubular structure, wherein the graphical representation comprises at least one indicator line representing the segmented portion's shape and/or extension. The graphical representation is displayed in combination with the image of the tubular structure. The display unit is further configured to display at least one marker overlaid to the image of the tubular structure. The interface unit is configured to position the marker at a location along the graphical representation to indicate a predetermined feature of the tubular structure.

According to an exemplary embodiment, the processing unit is configured to generate and initially position the at least one marker automatically next to the graphical representation.

According to an example, the processing unit is configured to restrict the movement possibilities of the marker in relation to the displayed image at least in one dimension, wherein the restriction is related to the graphical representation.

According to a third aspect of the present invention, a medical X-ray imaging system is provided, comprising an X-ray image acquisition arrangement with an X-ray source and an X-ray detector, and an annotating device according to the above mentioned aspect. The X-ray image acquisition arrangement is configured to provide an image of a tubular structure.

According to an aspect of the invention, a marker is shown together with a medical image. By providing a graphical representation of a segmented portion of the tubular structure, the user is provided with primary information about the examined situation, for example the vascular structure of a patient. In the latter case, i.e. if the tubular structure is a vascular structure, the segmented portion is a segmented vessel. In order to further determine tubular branches, such as vessel branches, and sub-branches, the user can visually identify respective image information provided by the medical image, and can then easily place the marker at the respective position. Before the positioning, the system may determine a location in the graphical representation with predetermined character or features, and initially position the marker next to this location in the graphical representation such that the user can right away start with the actual positioning by moving the marker along the graphical representation, such that any cumbersome positioning of a marker, i.e. hitting the graphical representation is omitted. The initial positioning may be based on a "best guess level" (see below). The movement control is facilitated in that the movement possibilities are restricted to a minimum. This is achieved by providing a marker that can only be moved by a sliding movement along the segmented portion structure, e.g. the segmented vessel structure, in form of the graphical representation. For example, in 2D, only a sliding movement along the portion of the tubular structure, e.g. the vessel, i.e. along a portion or vessel line so-to-speak in a backward and forward manner. In case of 3D-images of the tubular structure, the movement of the marker is possible in form of a sliding movement along the portion, e.g. the vessel, similar to that in a 2D-image, but the marker can also be rotated around the respective portion axis, such as the vessel axis, in order to determine spatial arrangement of a side branch, for example. However, also in 3D, the movement possibilities of the marker are restricted at least by one dimension. Instead of identifying sub-branches or bifurcations in a tubular structure such as a vessel structure, it is also possible to identify predetermined features, such as suspicious calcifications, lesions or others as mentioned above, which is facilitated and thus enhanced due to the restricted movement possibilities allowing the user a faster and less concentration requiring marker setting on a medical image. The identification of predetermined features may also be provided as an alternative, i.e. as an addition to the identification of sub-branches or bifurcations. For example, a clinician, such as a surgeon, can slide a marker along a segmented portion, such as a vessel, and can identify predetermined features while so-to-speak walking along the portion, e.g. the vessel. This steering or movement control is provided in a very straight forward manner, since for the navigation, only an up-and-down button is provided, for example on a tableside module, a bedside mouse, or by other means of providing input to a system.

These and other aspects of the invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
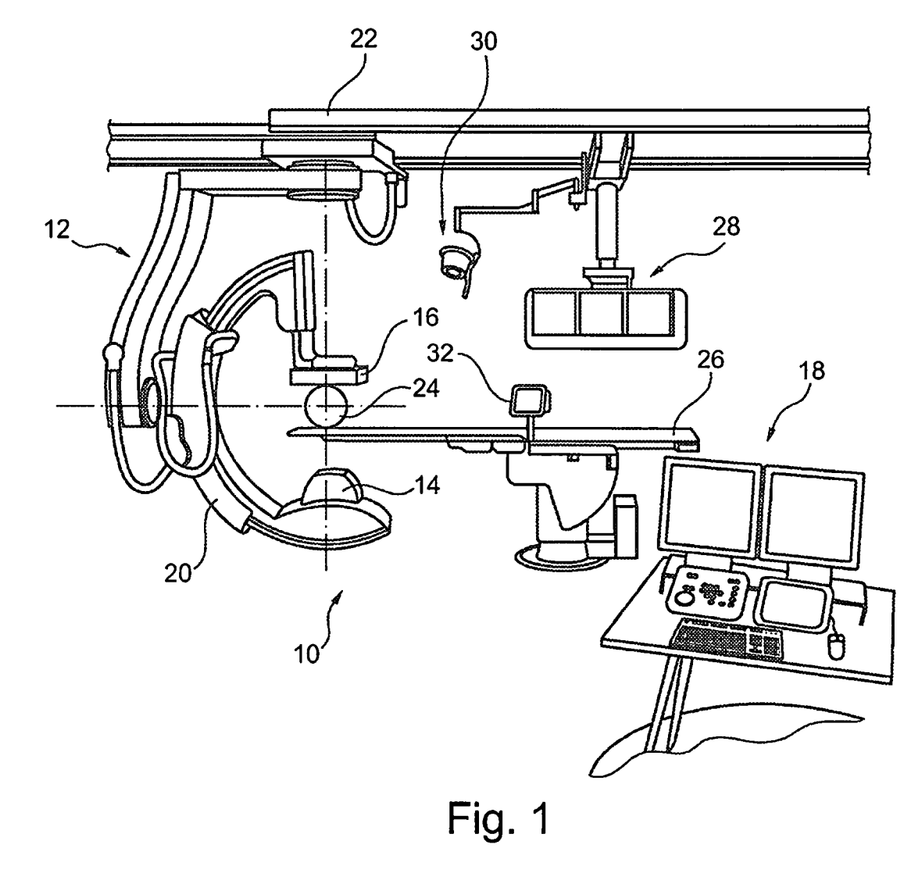
FIG. 1 schematically shows a medical X-ray imaging system according to an exemplary embodiment of the invention.

FIG. 1 shows a medical X-ray imaging system 10, comprising an X-ray image acquisition arrangement 12 with an X-ray source 14 and an X-ray detector 16. Further, an annotating device 18 is shown, which annotating device 18 shall be explained in more detail with reference to the following drawings.

The X-ray image acquisition arrangement 12 is shown as a so-called C-arm structure where the X-ray source 14 and the X-ray detector 16 are mounted to opposing ends of a movable C-arm structure 20. The C-arm structure 20 is movably mounted to a ceiling support 22 with a number of slideable and rotatable mounting support structures, which shall not be discussed any further, allowing rotational movement of the X-ray source and the X-ray detector around an object of interest, for example a patient, indicated with a spherical object 24. For supporting the object, for example the patient 24, a table 26 is provided that may be equipped with position adapting possibilities, i.e. with the possibility to adjust the height and the position of the table.

Further, a display arrangement 28 is provided in the vicinity of the table. Further, a lamp structure 30 is schematically indicated, as well as a first control interface 32 for operating the respective components of the X-ray image acquisition arrangement and other devices shown.

The X-ray image acquisition arrangement 12 is configured to provide an image of a tubular structure of a patient, for example.

According to an aspect of the invention, the tubular structure is a vascular structure and the segmented portion is a segmented vessel.

Figure 2:
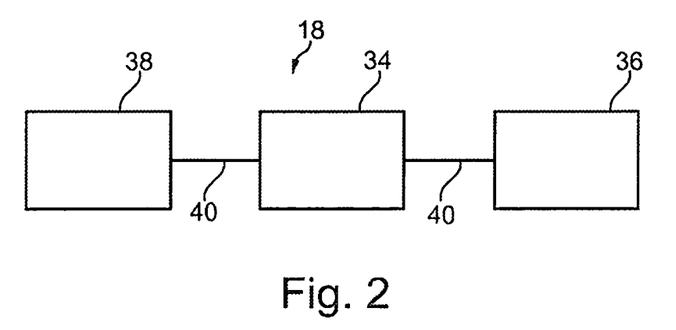
FIG. 2 schematically shows an annotating device for annotating a medical image according to an exemplary embodiment of the invention.

As shown in FIG. 2, the annotating device 18 comprises a processing unit 34, a display unit 36, and an interface unit 38. The processing unit 34, the display unit 36, and the interface unit 38 are schematically shown as being connected by connecting lines 40. It must be noted that the interface unit 38 may also be directly connected to the display unit 36. Of course, the display unit 36 can also be connected to the interface unit 38 instead of being connected to the processing unit 34.

The processing unit 34 is configured to generate at least one marker overlaid to an image of a tubular structure, wherein the marker is movable along the graphical representation.

The display unit 36 is configured to display an image of a tubular structure, and to display a graphical representation of the at least one segmented portion of the tubular structure. The graphical representation comprises at least one indicator line representing the portion's shape and/or extension, and the graphical representation is displayed in combination with the image of the tubular structure. The display unit 36 is further configured to display at least one marker overlaid to the image of the tubular structure.

The interface unit 38 is configured to position the marker at a location along the graphical representation to indicate a predetermined feature of the tubular structure.

For example, the processing unit 34 is configured to restrict the movement possibilities of the marker in relation to the displayed image at least in one dimension, wherein the restriction is related to the graphical representation.

Figure 3:
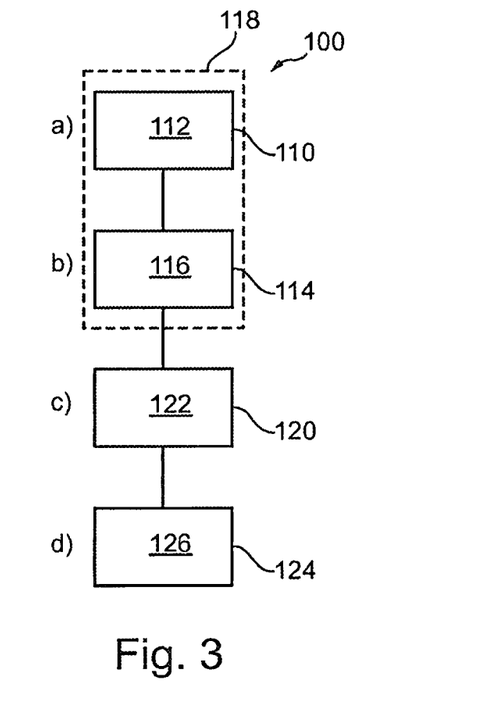
FIG. 3 schematically shows basic steps of a method for annotating a medical image according to an exemplary embodiment of the present invention.

With reference to FIG. 3, a method 100 for annotating a medical image is provided, comprising the following steps: In a first display step 110, an image of a tubular structure 112 is provided. In a second display step 114, a graphical representation 116 of at least one segmented portion of the tubular structure is displayed. The graphical representation comprises at least one indicator line representing the portion's shape and/or extension. The graphical representation is displayed in combination with the image of the tubular structure, which is indicated in FIG. 3 with an enclosing dotted rectangular box 118, indicating that the first and second display steps 110, 114 are provided in an at least partly temporally overlapping manner. In a further step, indicated with reference numeral 120, at least one marker is generated and displayed overlaid to the image of the tubular structure, wherein the marker is movable along the graphical representation. The at least one marker is indicated with reference numeral 122 in FIG. 3. Further, in a positioning step 124, the marker is positioned at a location along the graphical representation to indicate a predetermined feature 126 of the tubular structure.

The first display step 110 is also referred to as step a), the second display step 114 as step b), the generating and displaying step 110 as step c), and the positioning step 124 as step d).

According to an aspect of the present invention, the movement possibilities of the marker in relation to the displayed image are restricted at least in one dimension, wherein the restriction is related to the graphical representation.

According to an example, the image is a 2D image and the movement possibilities are restricted to one dimension only, namely back and forth along the segmented portion of the tubular structure. This requires minimal user interaction in form of entering two different commands only, which can be achieved with a simple interface such as a two-way switch, e.g. with a neutral intermediate position. For further reduction, a single command for moving along the segmented portion would be sufficient if a loop-function is provided enabling the return to the starting point, for example, the outmost beginning point of the segmented portion could, in order to reach positions once again.

According to another example, the image is a 3D image and the movement possibilities are restricted to two dimensions only, namely back and forth along the segmented portion of the tubular structure and rotating around the axis of the segmented portion. This requires minimal user interaction in form of entering two different commands for the movement along the segment, and two different commands for the movement around the axis, the latter also possible in form of only one command, due to complete rotation to reach positions once again For example, the movement along the graphical representation is controlled by a two-signal interface. For example, the user can move the marker along the portion outline using up and down buttons on a tableside module, with a bedside mouse, or other means of providing similar input to the system in form of two signals, since the marker can only move along the line, i.e. in two different directions along the portion of the tubular structure, such as along the vessel.

The marker may be movably attached to the graphical representation. For example, during the positioning, the marker is adhered to the graphical representation with an anchor point, wherein the anchor point is movable along the segmented portion.

For the positioning in the image plane, the marker is slideable along the graphical representation.

In case of positioning the marker in 3D, the marker can be rotatable around the axis of the segmented portion.

Figure 4:
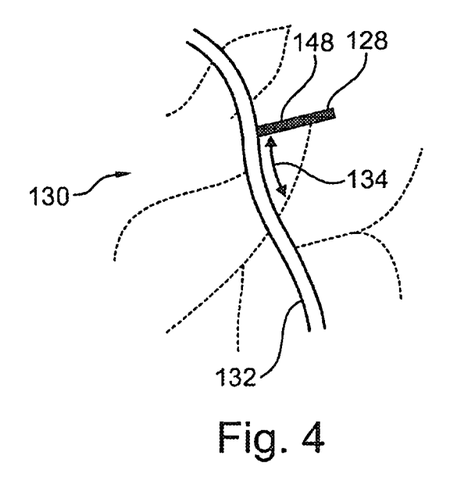
FIG. 4 shows a 2D-image of a vascular structure as an example for a tubular structure, in combination with a graphical representation and a 2D-marker, according to an embodiment of the invention.

According to a further embodiment, shown in FIG. 4, the marker 122 is a 2D-marker 128. The 2D-marker has, for example, a perpendicular orientation in relation to the respective portion of the at least one segmented portion, and is slideable along the portion. As can be seen in FIG. 4, an image 130 of a vascular structure as an example for a tubular structure is displayed. Further, a graphical representation 132 of a segmented vessel of the vascular structure is shown, which is indicated with through lines in FIG. 4, representing the segmented vessel, and dotted lines representing the vascular structure in the image.

It is noted that, although at least some of the embodiments refer to a vascular structure as an example for a tubular structure, the present invention is also provided for other tubular structures, such as air tracks or urinal tracks of a patient (not further shown). In particular, the features described with reference to the embodiments showing a vascular structure also apply for other tubular structures.

The movement possibilities of the 2D-marker are indicated with a double arrow 134.

Figure 5:
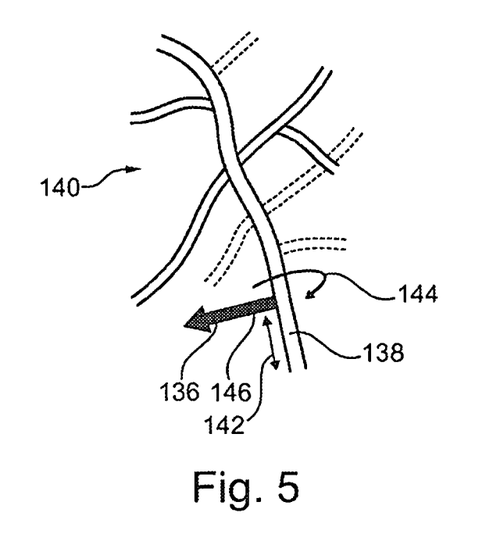
FIG. 5 shows a 3D-image of a vascular structure with a 3D-marker, and a graphical representation according to an exemplary embodiment of the invention.

According to a further exemplary embodiment, the marker 122 is a 3D-marker arrow 136 that has a spatial orientation in relation to a segmented vessel 138 (or portion) in case the image of the vascular (tubular) structure is a 3D-image 140, as shown in FIG. 5. The 3D-marker arrow 136 is slideable along the vessel, which is indicated with double arrow 142, and also rotatable around the vessel, which is indicated with circular arrow 144.

For example, the 3D-marker arrow 136 comprises at least a portion 146 perpendicular to the tubular's portion axis or centreline (not further shown).

With reference to FIG. 4, also the 2D-marker 128 may comprise at least one marker portion 148 perpendicular to the vessel outline. For example, the portion can be a line segment.

In 2D, as well as in 3D, the marker is movable only along the graphical representation, i.e. the movement possibilities are restricted to a movement along the graphical representation, for example along the outline or rotating around the centreline.

Thus, a user does not need to place the cursor at a respective portion point, which includes aiming at the outline of the portion in a manual manner, for example by a trackball or mouse. The present invention rather provides a possibility to enter simple commands to move along the portion. This is achieved by providing a marker, which so-to-speak magnetically sticks to the representation of the segmented portion. Thus, it is not necessary to place the marker exactly at the portion, but only to move it in the longitudinal direction. For example, the predetermined feature may be a bifurcation, for example of a sub-branch of the vascular structure, as an example for a tubular structure, as indicated in FIGS. 4 and 5.

According to the present invention, it is also provided that, in case the tubular structure is a vascular structure, the predetermined feature is at least one of the group of an aneurysm, a calcification within the vascular structure, a device placed inside the vascular structure, a dissection of the vessel, a lesion, a stenosis, and a thrombosis (not further shown).

Figure 6:
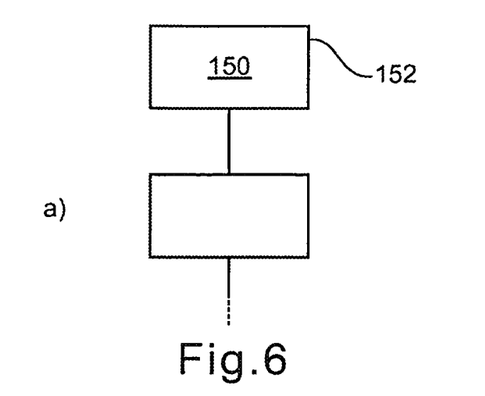
FIGS. 6 to 8 show further examples of methods for annotating a medical image according to exemplary embodiments of the invention.

In case of identifying different features in one medical image, different marker types may be provided for the respective different features. According to a further example, shown in FIG. 6, before step a), an image 150 of the tubular structure is acquired in an acquisition step 152 with an X-ray imaging modality.

The image of the vascular structure may be an X-ray image showing a vascular structure at least partly in a contrast medium injected state of the vessel structure under examination. Contrast medium can also be used in relation with air tracks and urinal tracks.

The image may be a 2D-image of the tubular structure.

Figure 7:
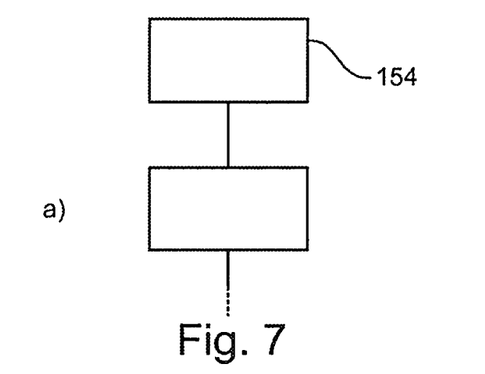

As shown in FIG. 7, the image provided to step a) may be a digital subtraction angiogram 154 of a vascular structure.

Figure 8:
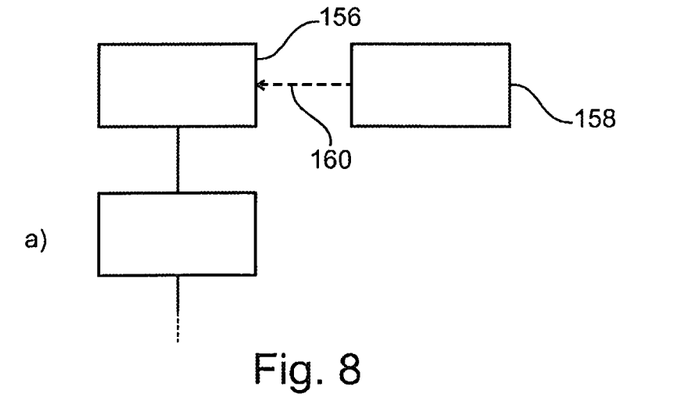

As already mentioned in relation with FIG. 5, the image may be a 3D-image 156 of the tubular, e.g. vascular structure. For example, the 3D-image is based on X-ray image data from the vascular structure. For example, the image data for the 3D-image is acquired by computed tomography 158, which is indicated in FIG. 8 with a dotted arrow 160, indicating that the CT (computed tomography) is only one possibility to provide 3D-image information.

Figure 9A:
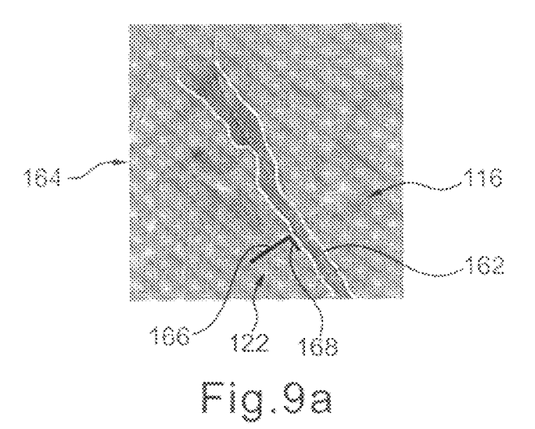
FIGS. 9a to 9c show a further example for a 2D-image of a vascular structure, with a graphical representation and a 2D-marker, according to an exemplary embodiment of the invention.
Figure 9B:
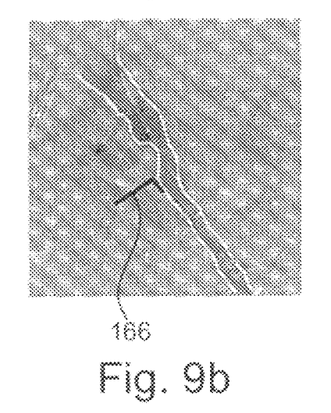
Figure 9C:
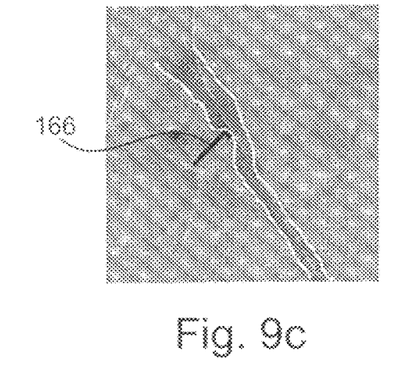

According to a further exemplary embodiment, shown in relation with FIGS. 9a to 9c, the segmented vessel is provided with a vessel outline 162.

FIG. 9a shows an X-ray based image, for example a fluoroscopy image 164 as the medical image. The vessel outline 162 is an example for a graphical representation 116, which may be overlaid to the fluoroscopy image 164. The at least one segmented vessel may comprise at least main vessel, for example aorta and/or common iliac. Thus, the graphical representation may comprise at least a path of the vessel. The graphical representation, for example the outline 162, may be displayed in overlaid manner 163 to the image of the vascular structure, as shown in FIGS. 9a to 9c. As can be seen in FIGS. 9a to 9c, besides the outlined segmented vessel, also further image information is provided, from which a clinician may derive sufficient information to determine, for example, a location of a bifurcation. It must be noted that the fluoroscopy image shown in FIGS. 9a to 9c is shown at least partly with injected contrast medium to visualize the vessel structure. However, it must be noted further, that it is also possible to provide other images showing the respective vessel structure information, for example fluoroscopy images without the use of contrast agent showing calcifications, implanted devices or other features.

With reference to FIG. 9a, the marker 122, which may also be referred to as an annotator, is shown with a main line segment 166 being arranged in a perpendicular manner to the segmented vessel and a base portion 168, which is perpendicular to the main section or main line portion 166, and which base portion or base element is aligned to the vessel outline. Thus, the base element may be a line segment, which is aligned to the orientation of the respective adjacent vessel outline segment. To identify predetermined features such as a bifurcation, the user can now enter a simple command to move the marker 122, or annotator, along the vessel outline 162. This is indicated in FIG. 9b, where the marker 166 is further along the vessel. In FIG. 9c, the marker 166 has arrived at a location being aligned with a branch to an anterior iliac, as an example for a side branch vessel.

In other words, according to an example of the present invention, initially the marker 166 may be placed automatically along the outline of the segmented vessel, which, for example, may be provided at a so-called "best guess" level.

The term "best guess" refers to the (automated or semi-automated) return of a computer algorithm designed to detect a particular feature of the tubular structure e.g. stenosis, heavy calcification, aneurysm etc. An illustrative example of a "best guess" is that provided by a computer program that automatically determines vessel bifurcation locations from contrast-enhanced runs during a stent-grafting procedure. This program returns the "best guess" level of the location and orientation of the bifurcation, which may then be displayed on a monitor for use during device navigation. While bifurcation detection works with high reliability for large vessels (e.g. aorta, common iliac), small aortic side-branch vessels are not always identified correctly; for example, the algorithm's "best guess" for the location of the ostium of the side-branch may be 2-3 cm from the actual location. This "best guess" will then require user adjustment in order for the marker location displayed to be clinically usable.

The user can then move the marker along the vessel outline using, for example, up and down buttons. The local direction of the outline is determined at the current position. The marker, for example consisting of a single line, is oriented perpendicular to the vessel outline. Once the marker has been moved by sliding to be aligned with a branch as detected by the clinician, it is further possible to enter a command to set a marker at the respective instance and to generate a further marker, for further indication purposes.

According to a further example, the marker is movable from one side of the graphical representation to the other side of the graphical representation, for example from one side of a vessel to another side of the vessel. Thus, the marker can be moved to a position where a feature is to be indicated. Such movement from one side to another can be achieved in a very easy manner, also requiring only minimal user interaction.

According to an aspect of the invention, only a minor amount of user interaction is needed, which helps to make annotating of vessel branches easy, for example, when full automatic segmentation is not accurate enough. This is achieved, for example, by providing a marker, which the clinician only needs to move along one axis instead of two axes, for example, which makes placement easier and more accurate. Movement along the segmented portions is thus facilitating the indication of detected features that should be marked manually. This provides great relief to the surgeon, for example, in particular compared with marking an image in the free space mode.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

What is claimed is:

1. An annotating device for annotating a medical image, the annotating device comprising:
   a display configured to display an image of a tubular structure and a graphical representation comprising an outline of a segmented portion of the tubular structure; and
   a processor configured to:
   generate a marker overlaid on the displayed image of the tubular structure, the marker movably attached to the graphical representation of the segmented portion of the tubular structure,
   receive commands to move the marker along the outline of the segmented portion of the tubular structure, while the marker remaining movably attached to the outline of the segmented portion of the tubular structure, wherein the commands for movement of the marker are restricted in at least one dimension to only move the marker by at least one of sliding of the marker along the attached outline of the segmented portion of the tubular structure and rotating of the marker around an axis of the segmented portion of the tubular structure, and
   based on the received commands, position the marker along the outline of the segmented portion of the tubular structure to indicate a feature of the tubular structure.

2. The annotating device according to claim 1, wherein the processor is further configured to:
   estimate the location of the feature of the tubular structure along the outline of the segmented portion based on determination of probabilities of the feature of the tubular structure being located at respective locations along the outline of the segmented portion,
   generate the marker overlaid on the displayed image of the tubular structure at the estimated location, and
   receive the commands to move the marker along the outline of the segmented portion to adjust the estimated location of the feature.

3. The annotating device according to claim 2, wherein the feature is a vessel bifurcation, and wherein the processor is configured to estimate the location of the feature of the tubular structure along the outline of the segmented portion based on determination of probabilities of the bifurcation being located at locations along the outline of the segmented portion and at an orientation.

4. The annotating device according to claim 1, wherein the marker is a 2D-marker with a fixed orientation relative to the segmented portion.

5. The annotating device according to claim 1, wherein the marker is a 3D-marker arrow with a spatial orientation relative to the segmented portion.

6. The annotating device according to claim 1, wherein the marker is movably attached to the graphical representation with an anchor point, which is movable along the graphical representation.

7. The annotating device according to claim 1, wherein the marker comprises an annotator having a main line segment arranged perpendicular to the segmented portion and a base portion arranged perpendicular to the main line segment, the base portion being aligned to the outline of the segmented portion.

8. A medical X-ray imaging system, comprising:
   an X-ray image acquisition arrangement with an X-ray source and an X-ray detector; and
   the annotating device according to claim 1;
   wherein the X-ray image acquisition arrangement is configured to provide the image of the tubular structure.

9. A method for annotating a medical image, comprising:
   displaying an image of a tubular structure;
   displaying a graphical representation overlaid on the image of the tubular structure, the graphical representation comprising an outline of a segmented portion of the tubular structure along a path of the tubular structure;
   generating and displaying a marker overlaid on the displayed image of the tubular structure, wherein the marker is movably adjoined to the graphical representation of the segmented portion of the tubular structure;
   receiving commands to move the marker along the outline of the segmented portion of the tubular structure, while the marker remaining movably adjoined to the outline of the segmented portion of the tubular structure, wherein the commands for movement of the marker are restricted to only move the marker by at least one of sliding of the marker along the adjoined outline of the segmented portion of the tubular structure and rotating of the marker around an axis of the segmented portion of the tubular structure; and
   based on the received commands, positioning the marker along the outline of the segmented portion of the tubular structure to indicate a feature of the tubular structure.

10. The method according to claim 9, wherein the marker is generated and initially positioned automatically.

11. The method according to claim 9, wherein the feature is at least one of:
    a bifurcation of a branch of the tubular structure;
    an aneurysm;
    a calcification within the tubular structure;
    a device placed inside the tubular structure;
    a dissection of the tubular structure;
    a lesion;
    a stenosis; and
    a thrombus.

12. The method according to claim 9, wherein the image of the tubular structure is a fluoroscopy image.

13. The method according to claim 9, wherein the image of the tubular structure is a 3D-image.

14. The method according to claim 9, wherein the tubular structure is a vascular structure and the segmented portion is a segmented vessel.

15. The method according to claim 9, wherein the marker is a 2D-marker with fixed orientation relative to the segmented portion.

16. The method according to claim 9, wherein the marker is a 3D-marker arrow with a spatial orientation relative to the segmented portion.

17. The method according to claim 9, further comprising:
    estimating the location of the feature of the tubular structure along the outline of the segmented portion based on determining probabilities of the feature of the tubular structure being located at respective locations along the outline of the segmented portion;
    generating the marker automatically overlaid on the displayed image of the tubular structure at the estimated location; and
    receiving the commands to move the marker along the outline of the segmented portion to adjust the estimated location of the feature.

18. The method according to claim 17, wherein the feature is a vessel bifurcation, and the method further comprises estimating the location of the feature of the tubular structure along the outline of the segmented portion based on determining probabilities of the bifurcation being located at respective locations along the outline of the segmented portion and orientations.

19. A non-transitory computer readable medium storing a computer program comprising instructions for annotating a medical image, the instructions, when executed by a processor, cause the processor to:
display an image of a tubular structure;
display a graphical representation overlaid on the image of the tubular structure, the graphical representation comprising an outline of a segmented portion of the tubular structure;
generate a marker overlaid on the displayed image of the tubular structure, wherein the marker is movably adjoined to the graphical representation of the segmented portion of the tubular structure;
receive commands to move the marker along the outline of the segmented portion of the tubular structure, while the marker remaining movably adjoined to the outline of the segmented portion of the tubular structure, wherein the commands for movement of the marker are restricted to only move the marker by at least one of sliding of the marker along the adjoined outline of the segmented portion of the tubular structure and rotating of the marker around an axis of the segmented portion of the tubular structure; and
based on the received commands, position the marker along the outline of the segmented portion of the tubular structure to indicate a feature of the tubular structure.

20. The non-transitory computer readable medium according to claim 19, further comprising instructions that, when executed by the processor, cause the processor to:
estimate the location of the feature of the tubular structure along the outline of the segmented portion based on determination of probabilities of the feature of the tubular structure being located at respective locations along the outline of the segmented portion,
generate the marker overlaid on the displayed image of the tubular structure at the estimated location, and
receive the commands to move the marker along the outline of the segmented portion to adjust the estimated location of the feature.

21. The non-transitory computer readable medium according to claim 20, wherein the feature is a vessel bifurcation, and the instructions, when executed by the processor, further cause the processor to estimate the location of the feature of the tubular structure along the outline of the segmented portion based on determination of probabilities of the bifurcation being located at respective locations along the outline of the segmented portion and orientations.

* * * * *